US00PP16934P2

(12) United States Plant Patent
Utecht

(10) Patent No.: US PP16,934 P2
(45) Date of Patent: Aug. 1, 2006

(54) ***PELARGONIUM* PLANT NAMED 'FISHELUS'**

(50) Latin Name: *Pelargonium×hortorum*
Varietal Denomination: Fishelus

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 22 days.

(21) Appl. No.: 11/167,717

(22) Filed: Jun. 27, 2005

(51) Int. Cl.
*A01H 5/00* (2006.01)

(52) U.S. Cl. ..... Plt./327
(58) Field of Classification Search ..... Plt./327
See application file for complete search history.

*Primary Examiner*—Kent Bell
(74) *Attorney, Agent, or Firm*—Jondle & Associates P.C.

(57) ABSTRACT

A new cultivar of *Pelargonium* particularly distinguished by its salmon-pink, semi-double flowers, large flower heads, intense green zonation of the foliage, and a medium sized plant habit is disclosed.

1 Drawing Sheet

Figure 1:
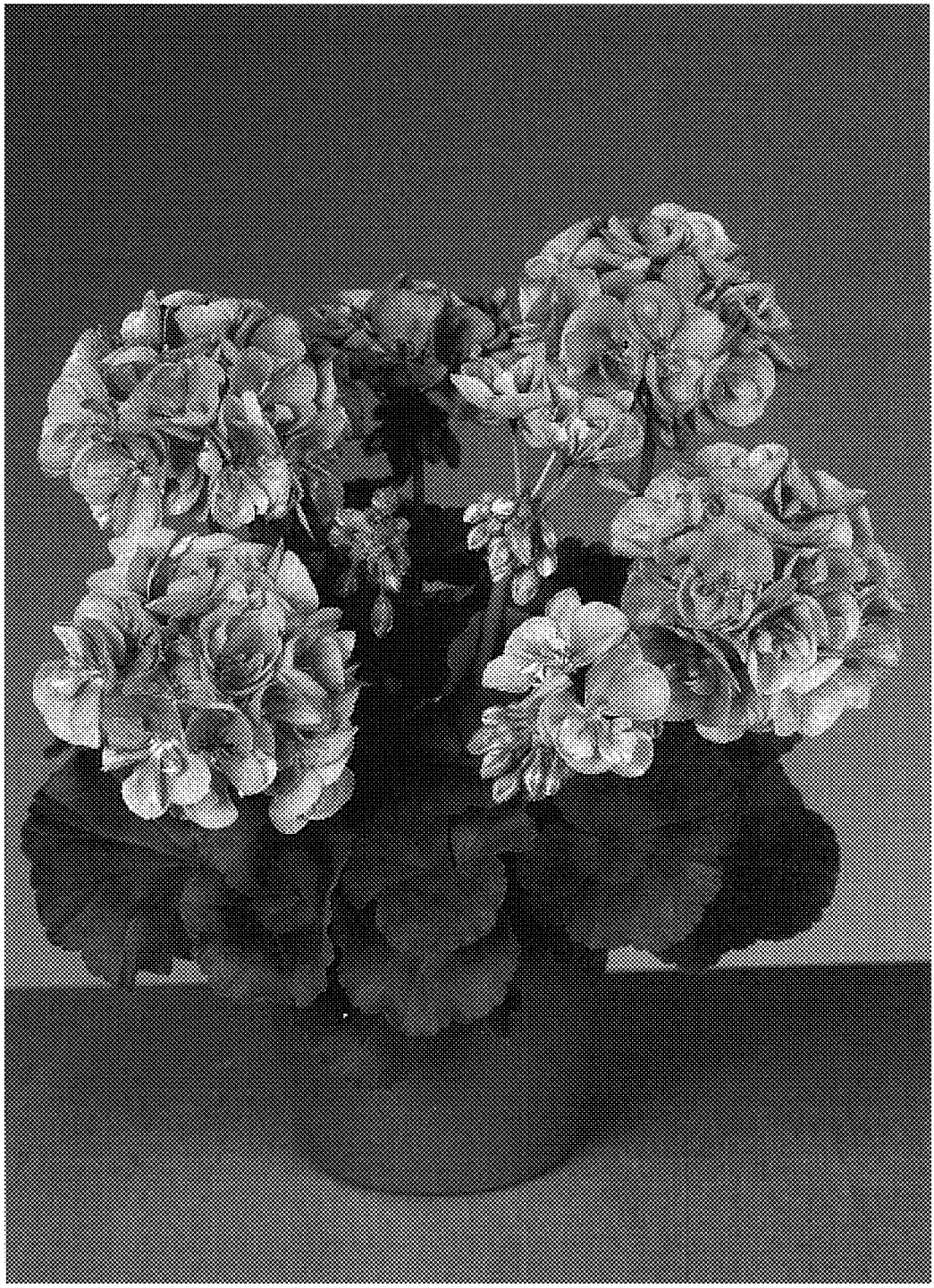

Genus and species: *Pelargonium×hortorum.*
Variety denomination: 'Fishelus'.

BACKGROUND OF THE NEW PLANT

The present invention comprises a new and distinct cultivar of *Pelargonium*, botanically known as *Pelargonium× hortorum*, resp. a hybrid of *Pelargonium zonale* L'Héritier and hereinafter referred to by the cultivar name 'Fishelus'. The new cultivar is a product of a planned breeding program which had the objective of creating new varieties having salmon-pink, semi-double flowers, large flower heads, and intense green zonation of foliage. 'Fishelus' was discovered as a seedling resulting from a cross between the female parent, hybrid seedling No. 91-1216-3 (unpatented), which has salmon-colored single-type flowers with medium green foliage and strong zonation, and the male parent, hybrid seedling No. i93-250-8 (unpatented), which has orange-red semi-double flowers, medium-green foliage with relatively strong zonation and a compact growth habit.

The new cultivar was created in 1995 in Hillscheid, Germany, and has been asexually reproduced repeatedly by vegetative cuttings in Galdar, Gran Canaria, Spain, and Hillscheid, Germany, over a nine-year-period. 'Fishelus' has not been observed under all possible environmental conditions, thus, the phenotype may vary significantly with variations in the environment such as temperature, light intensity, and day length. It has been found to retain its distinctive characteristics through successive asexual propagations. 'Fishelus' reproduces true to type in successive generations of asexual reproduction.

Plant Breeder's Rights for this cultivar were applied for in Germany on Jun. 2, 2004. No sales or offers for sale of this cultivar have been made before early July 2004.

SUMMARY OF THE INVENTION

The following are the most outstanding and distinguishing characteristics of this new cultivar when grown under normal horticultural practices in Hillscheid, Germany.

1. Salmon-pink, semi-double flowers;
2. Large inflorescences on strong peduncles high above the foliage;

3. Medium-green foliage and large leaves with distinct zonation;
4. Moderately vigorous growth with no shattering (dropping of petals);
5. Tall and rounded with a moderately wide plant habit;
6. Early to mid-spring flowering response; and
7. Fair rain resistance.

DESCRIPTION OF PHOTOGRAPH

This new *geranium* plant is illustrated by the accompanying photograph which shows blooms, buds, and foliage of the plant; the colors shown are as true as can be reasonably obtained by conventional photographic procedures. The photograph is of a twelve-week-old plant grown from rooted cuttings in 14-cm pots, left un-pinched, and grown under greenhouse conditions which approximate those generally used in commercial practice.

FIG. 1. shows overall plant habit with blooms, buds, and foliage.

DESCRIPTION OF THE NEW CULTIVAR

The following detailed descriptions set forth the distinctive characteristics of 'Fishelus'. The data which define these characteristics were collected from asexual reproductions carried out in Hillscheid, Germany. The plant history was taken on twelve-week-old, un-pinched plants in 14-cm pots in a greenhouse during mid-May. The color readings were determined under natural light in mid-May from flowers grown in a greenhouse. Color references are to The R.H.S. Colour Chart of The Royal Horticultural Society of London (R.H.S.) (2001).

DETAILED BOTANICAL DESCRIPTION

Classification:

*Botanical.*—*Pelargonium×hortorum*, resp. a hybrid of *Pelargonium zonale* L'Héritier.

*Common name.*—*Geranium.*

*Parentage.*—Female parent: Hybrid seedling No. 91-1216-3 (unpatented). Male parent: Hybrid seedling No. i93-250-8 (unpatented).

Plant:
*Form*.—Rounded.
*Branching habit*.—6.0 branches per plant.
*Height*.—15.3 cm for a 9 week-old plant (measured from base of stem to the tips of the branches, excluding the inflorescences).
*Width*.—24.8 cm for a 9 week-old plant.
*Time to produce a finished flowering plant*.—For spring flower response in Hillscheid, Germany, in 2004, 50% of the plants had begun flowering 8 weeks after being planted from rooted cuttings.
*Outdoor plant performance*.—Plants continuously flower; a flower count in mid-May of 2004 in Hillscheid, Germany indicated about 3.2 inflorescences per plant.

Leaves:
*Arrangement*.—Alternate.
*Immature leaf*.—Color: (medium green). Upper surface: RHS 137C (medium-green) to RHS 137D (medium-green). Lower surface: RHS 137D (medium green).
*Mature leaf*.—Color: Upper surface: RHS 137C to RHS 137D (medium-green). Lower surface: RHS 137D (medium-green). Length: 5.8 cm. Width: 9.8 cm.
*Zonation color*.—RHS 166A (brown) with a medium distinctness.
*Zonation diameter*.—Inner diameter is 4.2 cm and width of the brown band is 2.0–2.2 cm.
*Apex*.—Rounded.
*Base*.—Cordate.
*Shape*.—Kidney-shaped to nearly round, with only very weak lobes, with the lowest lobes overlapping or being divided by a narrow gap.
*Margin*.—Bi-crenate.
*Texture*.—Upper surface is smooth, dull, and velvety.

Petioles:
*Length*.—5.0–6.0 cm.
*Diameter*.—0.3 cm.
*Color*.—RHS 143C (light-green).
*Texture*.—Slightly pubescent.

Stems:
*Length*.—9.0–12.0 cm.
*Internode length*.—1.0–1.5 cm.
*Color*.—RHS 143B (light-green).
*Texture*.—Appears smooth with weak pubescence.

Flower buds:
*Length*.—1.7 cm.
*Width*.—1.0 cm.
*Shape*.—Elliptical.
*Color of sepals* (*just before petals unfold*).—RHS 144A (light-green).
*Color of petals* (*just before petals unfold*).—RHS 41B to RHS 43D.

Inflorescence:
*Type*.—An umbel composed of 35–45 flowers.
*Umbel diameter*.—10.8 cm.
*Umbel depth* (*height*).—6.0 cm.
*Umbel shape*.—Semi-spherical.
*Lastingness of umbel on the plant*.—16 days.
*Peduncle*.—Length: 14.8 cm. Diameter: 3.0–4.0 mm. Texture: Weak pubescence. Color: RHS 144B (light-green).
*Pedicel*.—Length: 2.9 cm. Diameter: 1.5 mm. Texture: Weak pubescence. Color: RHS 144B (light-green); and near upper end occasionally brownish infused, near RHS 179B.

Corolla:
*Diameter*.—4.8 cm.
*Form*.—Semi-double.
*Shape*.—Round outline, with the upper petals nearly the same size and shape as the lower petals which are cup-shaped.
*Number of petals*.—6–9.
*Petaloids*.—Number: 0–2. Shape: Narrow. Color: RHS 40A to RHS 40B.
*Lastingness of individuals flowers on the plant*.—8 days at 18° C.
*Fragrance*.—None.

Petals:
*Upper petals*.—Length: 2.9–3.0 cm. Width: 2.2–2.4 cm. Color: Upper surface: RHS 41B for the base, RHS 43D near margin and upper part; the color may change to RHS 52D (pink) while maturing. Lower surface: RHS 43D but somewhat variable. Markings: RHS 47B (pink) very fine veins.
*Lower petals*.—Length: 2.5–2.6 cm. Width: 2.1–2.2 cm. Color: Upper surface: Mainly RHS 41B. Lower surface: RHS 43D but somewhat variable. Markings: Absent.
*Shape*.—Obovate.
*Apex*.—Rounded.
*Base*.—Acute.
*Margin*.—Entire or slightly crenated at the tip.
*Texture*.—Smooth, glabrous and slightly glossy.

Sepals:
*Number*.—5.
*Length*.—1.0–1.2 cm.
*Width*.—0.4 cm for largest upper sepal, 0.2 cm for the other sepals.
*Shape*.—Linear to lanceolate.
*Apex*.—Acute.
*Base*.—Truncate.
*Margin*.—Entire.
*Texture*.—Very weak pubescence.
*Color*.—For both the upper and lower surfaces, RHS 144B (light-green) and near base is weakly RHS 179B (brown).

Reproductive organs:
*Androecium*.—Number of anthers: 2–5. Filament color: RHS 155D (white). Filament length: 4.0–5.0 mm. Pollen color: RHS 26A (yellow-orange). Pollen amount: Moderate.
*Gynoecium*.—Pistil number: 1. Pistil length: 8.0 mm. Stigma color: RHS 43D (salmon-pink). Stigma shape: 5–6 lobed. Style color: RHS 43D (salmon-pink). Style length: 3.0 mm. Style shape: Filiform with the stigma lobes at right angles.

Fruit/seed set: A few seeds may develop.

Disease and insect resistance: Average and typical for the species.

COMPARISON WITH KNOWN CULTIVARS

Of the many commercial cultivars known to the present inventor, the most similar in comparison to 'Fishelus' are the varieties 'Schöne Helena' (U.S. Plant Pat. No. 5,374) and 'Fishelen' (U.S. Plant Pat. No. 12,727).

Cultivar 'Fishelus' differs from the female parent hybrid seedling No. 91-1216-3 (unpatented) in that 'Fishelus' has semi-double flowers and intense green and zoned foliage while hybrid seedling No. 91-1216-3 has single-type flowers and medium-green foliage with strong zonation.

Cultivar 'Fishelus' differs from the male parent hybrid seedling No. i93-250-8 (unpatented) in that 'Fishelus' has salmon-pink flowers while hybrid seedling No. i93-250-8 has orange-red flowers.

Cultivar 'Fishelus' differs from the commercial comparison variety 'Schöne Helena' (U.S. Plant Pat. No. 5,374) in that 'Fishelus' has salmon-pink flowers while 'Schöne Helena' has salmon-pink and white semi-double flowers with several inner petals. The inflorescences of 'Fishelus' are about 1.0 cm smaller in diameter than those of 'Schöne Helena' but 'Fishelus' develops twenty-percent more flowers than 'Schöne Helena'. Additionally, 'Fishelus' displays about medium distinct zonation of the leaves while 'Schöne Helena' has weak zonation of the leaves.

Cultivar 'Fishelus' differs from the commercial comparison variety 'Fishelen' (U.S. Plant Pat. No. 12,727) in that 'Fishelus' has semi-double flowers while 'Fishelen' has nearly single-type flowers. Additionally, 'Fishelus' displays about medium distinct zonation of the leaves while 'Fishelen' has strong zonation of the leaves.

I claim:

1. A new and distinct cultivar of *Pelargonium* plant as shown and described herein.

* * * * *